US00RE39561E

(19) United States
(12) Reissued Patent
Winter et al.

(10) Patent Number: US RE39,561 E
(45) Date of Reissued Patent: Apr. 10, 2007

(54) METALLOCENES CONTAINING LIGANDS OF 2-SUBSTITUTED INDENYL DERIVATIVES, PROCESS FOR THEIR PREPARATION, AND THEIR USE AS CATALYSTS

(75) Inventors: Andreas Winter, Neuleiningen (DE); Martin Antberg, Hofheim am Taunus (DE); Walter Spaleck, Bremen (DE); Jürgen Rohrmann, Kelkheim (DE); Volker Dolle, Bensheim (DE)

(73) Assignee: Basell Polyoefine GmbH (DE)

(21) Appl. No.: 08/895,950

(22) Filed: Jul. 17, 1997

Related U.S. Patent Documents

Reissue of:
(64) Patent No.: 5,276,208
Issued: Jan. 4, 1994
Appl. No.: 07/789,361
Filed: Nov. 8, 1991

U.S. Applications:
(62) Division of application No. 08/324,260, filed on Oct. 17, 1994, now Pat. No. Re. 37,208.

(30) Foreign Application Priority Data

Nov. 12, 1990 (DE) ..... 4035884

(51) Int. Cl.
*C07F 7/28* (2006.01)
*C07F 9/00* (2006.01)
*C07F 11/00* (2006.01)

(52) U.S. Cl. ..... 556/53; 556/9; 556/11; 556/14; 556/19; 556/21; 556/22; 556/43; 556/58; 526/129; 526/160; 502/117; 502/152

(58) Field of Classification Search ..... 556/9, 556/11, 14, 19, 21, 22, 43, 53, 58; 502/117, 502/152, 103, 154; 526/129, 160, 943, 127, 526/132
See application file for complete search history.

(56) References Cited

U.S. PATENT DOCUMENTS

| | | | | |
|---|---|---|---|---|
| 4,769,510 A | * | 9/1988 | Kaminsky et al. | 585/512 |
| 4,871,705 A | * | 10/1989 | Hoel | 526/904 |
| 4,892,851 A | | 1/1990 | Ewen et al. | |
| 4,931,417 A | | 6/1990 | Miya et al. | |
| 5,017,714 A | | 5/1991 | Welborn, Jr. | |
| 5,087,677 A | | 2/1992 | Brekner et al. | |
| 5,103,030 A | | 4/1992 | Rohrmann et al. | |
| 5,145,819 A | | 9/1992 | Winter et al. | |
| 5,243,001 A | | 9/1993 | Winter et al. | 526/127 |
| 5,276,208 A | | 1/1994 | Winter et al. | |
| 5,278,264 A | | 1/1994 | Spaleck et al. | |
| 5,296,434 A | | 3/1994 | Karl et al. | |
| 5,324,800 A | | 6/1994 | Welborn, Jr. | 526/160 |
| 5,329,033 A | | 7/1994 | Spaleck et al. | 556/53 |
| 5,455,365 A | | 10/1995 | Winter et al. | |
| 5,561,093 A | | 10/1996 | Fujita et al. | 502/117 |
| 6,143,911 A | | 11/2000 | Fujita et al. | 556/11 |

FOREIGN PATENT DOCUMENTS

| | | | |
|---|---|---|---|
| DE | 37 26 067 | | 2/1989 |
| DE | 3 826 075 | | 2/1990 |
| DE | 3826075 | * | 2/1990 |
| DE | 40 35 886 | | 11/1990 |
| DE | 41 28 238 | | 8/1991 |
| DE | 0 284 708 | | 10/1998 |
| EP | 0 129 368 | | 12/1984 |
| EP | 0 185 918 | | 7/1985 |
| EP | 0 316 155 | | 5/1989 |
| EP | 0 320 762 | | 6/1989 |
| EP | 0 336 128 | | 10/1989 |
| EP | 0344887 | * | 12/1989 |
| EP | 0 344 887 | | 12/1989 |
| EP | 0 347 129 | | 12/1989 |
| EP | 0 351 392 | | 1/1990 |
| EP | 0 355 289 | | 2/1990 |

(Continued)

OTHER PUBLICATIONS

Spaleci et al., New J. Chem., "Stereorigid Metallocenes: Correlations Between Structure and Behavior in Homopolymerizations of Propylene", vol. 14, pp. 499–503, 1990.*
JACS (1967) 89(23) 5868–5876, Nov. 1967.*

(Continued)

*Primary Examiner*—Fred Teskin
(74) *Attorney, Agent, or Firm*—Connolly Bove Lodge & Hutz

(57) ABSTRACT

The novel metallocenes of the formula I (I)

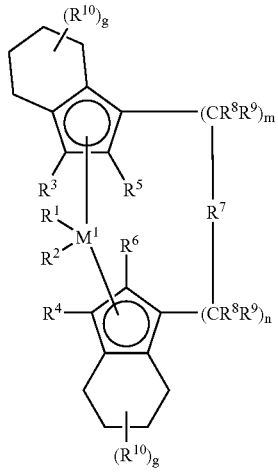

in which, preferably, $M^1$ is Zr or Hf, $R^1$ and $R^2$ are alkyl or halogen, $R^3$ and $R^4$ are hydrogen, $R^5$ and $R^6$ are alkyl or haloalkyl, $—(CR^8R^9)_m—R^7—(CR^8R^9)_n—$ is a single- or multi-membered chain in which $R^7$ may also be a (substituted) hetero atom, m+n is zero or 1, and $R^{10}$ is hydrogen, form, together with aluminoxanes as cocatalysts, a very effective catalyst system for the preparation of polyolefins of high stereospecificity and high melting point.

23 Claims, No Drawings

FOREIGN PATENT DOCUMENTS

| | | | | |
|---|---|---|---|---|
| EP | 0 366 290 | | 5/1990 | |
| EP | 0 407 870 | | 1/1991 | |
| EP | 0 426 643 | | 5/1991 | |
| EP | 0 433 990 | | 6/1991 | |
| EP | 442 725 | | 8/1991 | |
| EP | 0 485 821 | | 5/1992 | |
| EP | 0 485 823 | | 5/1992 | |
| EP | 0 500 005 | | 8/1992 | |
| EP | 0 529 908 | | 3/1993 | |
| JP | 62-121707 | * | 6/1987 | ..... 526/160 |

OTHER PUBLICATIONS

BULLETIN DE LA SOCIETE CHIMIQUE DE FRANCE, "*Etude de monomeres halogenes et de leur polymerisation cationique*", No. 11, pp. 3092–3095, (1973).

J. ORG. CHEM., "*Friedel–Crafts Reactions of Ethyl Cyclopropanecarboxylate*", vol. 46, pp. 3758–3760 (1981).

Soga, K. et al., MACROMOLECULES, "*Perfect Conversion of Aspecific Sites into Isopecific Sites in Ziegler–Natta Catalysts*", vol. 22, pp. 3824–3826 (1989).

J. ORG. CHEM., "*Friedel–Crafts Chemistry, A Mechanistic Study of the Reaction of 3–Chloro–4'–fluoro–2–methylpropiophenone with* $AlCl_3$ *and* $AlCl_3$–$CH_3NO_2$", vol. 43, No. 16, pp. 3126–3131 (1978).

Spaleck et al., NEW J. CHEM., "*Stereorigid Metallocenes: Correlations Between Structure and Behaviour in Homopolymerizations of Propylene*", vol. 14, pp. 499–503 (1990).

Röll, V.W., et al., ANGEW. CHEM., "*Stereo– und Regioselektivitat von chiralen, alkylsubstituierten ansa–Zirconocen–Katalysatoren bei der Methylalumoxan–aktivierten Propen–Polymerization*", vol. 102, No. 3, pp. 339–341 (1990).

Piccoliovazzi, N. et al., ORGANOMETALLICS, "*Electronic Effects in Homogeneous Indenylzirconium Ziegler–Natta Catalysts*", vol. 9, pp. 3098–3105 (1990).

Chemical Abstracts 90:567 103691p; (1978).

Criegee et al., *Chem. Ber.,* vol. 94, "*Uber den Nickelkomplex* $C_{18}H_{22}Ni$ *und den daraus gewonnenen Kohlenwasserstoff* $C_{13}H_{18}$", pp. 3461–3468 (1964).

Hart et al., NOTES, *J. Am. Chem. Soc.,* vol. 72, "*Acylation–Akylation Studies*", pp. 3286–3287 (1950).

Katz, Thomas J., *J. Am. Chem. Soc.,* "Asymmetric Synthesis of Helical Metallocenes", vol. 108, 1986, pp. 179–181.

Ewen, J.A., et al, *J. Am. Chem. Soc.,* Crystal Structures and Sterospecific Propylene Polymerizations with Chiral Hafnium Metallocene Catalysts, vol. 109, 1987, pp. 6544–6545.

Miyamota, T.K., et al., CHEMISTRY LETTERS, The Chemical Society of Japan, "*A Bulky Ligand and its Organometallic Compound: Synthesis of Heptamethylidene and a Ferrocene–Type Complex,* $Fe(n^5–C_9Me_7)_2$", pp. 729–730 (1981).

Esperas, S., ACTA CHEMICA SCANDINAVICA, "*The Crystal and Molecular Structure of Cyano(methylisocyanide)gold(I)*", A 30, No. 7, pp. 527–530 (1976).

Adcock et al., *Austr. J. Chem.,* vol. 29, "*Substituent Effects by* $^{19}F$ *Nuclear Magnetic Resonance: Polar and* $\pi$*–Electron Effects*", pp. 2571–2581.

Marechal et al., *Bull. Soc. Chim. Fr. 6, "Homopolymerisation cationlique des dimethyl–4,7,dimethyl–4,6 et dimethyl–5,6 indenes",* No. 348, pp. 1981–2039, (1969).

*Winter* v. *Fujita,* 53 U.S.P.Q.2d 1234 (Bd of Appeals 1999).

*Winter* v. *Fujita,* 53 U.S.P.Q.2d 1478 (Bd of Appeals 2000).

* cited by examiner

METALLOCENES CONTAINING LIGANDS OF 2-SUBSTITUTED INDENYL DERIVATIVES, PROCESS FOR THEIR PREPARATION, AND THEIR USE AS CATALYSTS

Matter enclosed in heavy brackets [ ] appears in the original patent but forms no part of this reissue specification; matter printed in italics indicates the additions made by reissue.

*This application is a voluntary division under* 37 C.F.R. 1.177 of copending reissue application Ser. No. 08/324,260, filed Oct. 17, 1994, now Re 37,208 E, both of which are reissues of U.S. Pat. No. 5,276,208 (application Ser. No. 07/789,361, filed Nov. 8, 1991).

The present invention relates to novel metallocenes which contain ligands of 2-substituted indenyl derivatives and can very advantageously be used as catalysts in the preparation of polyolefins of high melting point (high isotacticity).

Polyolefins of relatively high melting point and thus relatively high crystallinity and relatively high hardness are particularly important as engineering materials (for example large hollow articles, tubes and moldings).

Chiral metallocenes are, in combination with aluminoxanes, active, stereospecific catalysts for the preparation of polyolefins (U.S. Pat. No. 4,769,510). These metallocenes also include substituted indene compounds. Thus, for example, the use of the ethylenebis(4,5,6,7-tetrahydro-1-indenyl)zirconium dichloride/aluminoxane catalyst system is known for the preparation of isotactic polypropylene; cf. EP-A 185 918). Both this and numerous other polymerization processes coming under the prior art have, in particular, the disadvantage that, at industrially interesting polymerization temperatures, only polymers of relatively low melting points are obtained. Their crystallinity and thus their hardness are too low for use as engineering materials.

Surprisingly, it has now been found that metallocenes which contain, as ligands, certain 2-substituted indenyl derivatives are suitable catalysts for the preparation of polyolefins of high isotacticity (melting point) and narrow molecular weight distribution.

The present invention therefore provides the compounds of the formula I below (I)

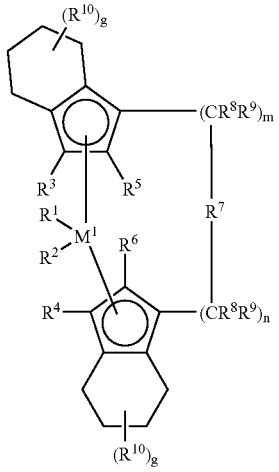

in which $M^1$ is a metal from group IVb, Vb or VIb of the Periodic Table, $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom, $R^3$ and $R^4$ are identical or different and are a hydrogen atom, a halogen atom, a $C_1$–$C_{10}$-alkyl group, which may be halogenated, a $C_6$–$C_{10}$-aryl group, an —$NR_2^{15}$, —$SR^{15}$, —$OSiR_3^{15}$, —$SiR_3^{15}$ or —$PR_2^{15}$ radical in which $R^{15}$ is a halogen atom, a $C_1$–$C_{10}$-alkyl group or a $C_6$–$C_{10}$-aryl group, $R^5$ and $R^6$ are identical or different and are as defined for $R^3$ and $R^4$, with the proviso that $R^5$ and $R^6$ are not hydrogen, $R^7$ is

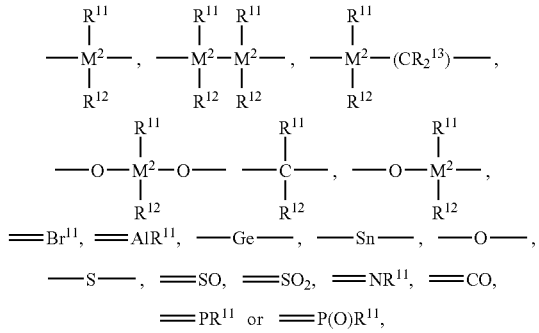

where $R^{11}$, $R^{12}$ and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{11}$ and $R^{12}$ or $R^{11}$ and $R^{13}$, in each case with the atoms connecting them, form a ring, $M^2$ is silicon, germanium or tin, $R^8$ and $R^9$ are identical or different and are as defined for $R^{11}$, m and n are identical or different and are zero, 1 or 2, m plus n being zero, 1 or 2, and, the radicals $R^{10}$ are identical or different and are as defined for $R^{11}$, $R^{12}$ and $R^{13}$.

Alkyl is straight-chain or branched alkyl. Halogen (halogenated) is fluorine, chlorine, bromine or iodine, preferably fluorine or chlorine.

In the formula I, $M^1$ is a metal from group IVb, Vb or VIb of the Periodic Table, for example titanium, zirconium, hafnium, vanadium, niobium, tantalum, chromium, molybdenum or tungsten, preferably zirconium, hafnium or titanium.

$R^1$ and $R^2$ are identical or different and are a hydrogen atom, a $C_1$–$C_{10}$-, preferably $C_1$–$C_3$-alkyl group, a $C_1$–$C_{10}$-, preferably $C_1$–$C_3$-alkoxy group, a $C_6$–$C_{10}$-, preferably $C_6$–$C_8$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$-, preferably $C_7$–$C_{12}$-alkylaryl group, a $C_8$–$C_{40}$-, preferably $C_8$–$C_{12}$-arylalkenyl group or a halogen atom, preferably chlorine.

$R^3$ and $R^4$ are identical or different and are a hydrogen atom, a halogen atom, preferably a fluorine, chlorine or bromine atom, a $C_1$–$C_{10}$-, preferably $C_1$–$C_4$-alkyl group, which may be halogenated, a $C_6$–$C_{10}$-, preferably $C_6$–$C_8$-aryl group, an —$NR_2^{15}$, —$SR^{15}$, —O—$SiR_3^{15}$, —$SiR_3^{15}$ or —$PR_2^{15}$ radical in which $R^{15}$ is a halogen atom, preferably a chlorine atom, or a $C_1$–$C_{10}$-, preferably $C_1$–$C_3$-alkyl group or a $C_6$–$C_{10}$-, preferably $C_6$–$C_8$-aryl group. $R^3$ and $R^4$ are particularly preferably hydrogen.

$R^5$ and $R^6$ are identical or different, preferably identical, and are as defined for $R^3$ and $R^4$, with the proviso that $R^5$ and $R^6$ cannot be hydrogen. $R^5$ and $R^6$ are preferably ($C_1$–$C_4$)-alkyl, which may be halogenated, such as methyl, ethyl, propyl, isopropyl, butyl, isobutyl or trifluoromethyl, in particular methyl.

$R^7$ is

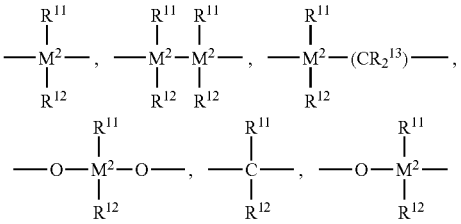

=$BR^{11}$, =$AlR^{11}$, —Ge—, —Sn—, —O—, —S—, =SO, =$SO_2$, =$NR^{11}$, =CO, =$PR^{11}$ or =$P(O)R^{11}$, where $R^{11}$, $R^{12}$ and $R^{13}$ are identical or different and are a hydrogen atom, a halogen atom, a $C_1$–$C_{10}$-, preferably $C_1$–$C_4$-alkyl group, in particular a methyl group, a $C_1$–$C_{10}$-fluoroalkyl group, preferably a $CF_3$ group, a $C_6$–$C_{10}$-, preferably $C_6$–$C_8$-aryl group, a $C_6$–$C_{10}$-fluoroaryl group, preferably a pentafluorophenyl group, a $C_1$–$C_{10}$-, preferably $C_1$–$C_4$-alkoxy group, in particular a methoxy group, a $C_2$–$C_{10}$-, preferably $C_2$–$C_4$-alkenyl group, a $C_7$–$C_{40}$-, preferably $C_7$–$C_{10}$-arylalkyl group, a $C_8$–$C_{40}$-, preferably $C_8$–$C_{12}$-arylalkenyl group or a $C_7$–$C_{40}$-, preferably $C_7$–$C_{12}$-alkylaryl group, or $R^{11}$ and $R^{12}$ or $R^{11}$ and $R^{13}$, in each case together with the atoms connecting them, form a ring.

$M^2$ is silicon, germanium or tin, preferably silicon or germanium.

$R^7$ is preferably =$CR^{11}R^{12}$, =$SiR^{11}R^{12}$, =$GeR^{11}R^{12}$, —O—, —S—, =SO, =$PR^{11}$ or =$P(O)R^{11}$.

$R^8$ and $R^9$ are identical or different and are as define as for $R^{11}$.

m and n are identical or different and are zero, 1 or 2, preferably zero or 1, where m plus n is zero, 1 or 2, preferably zero or 1.

The radicals $R^{10}$ are identical or different and are as defined for $R^{11}$, $R^{12}$ and $R^{13}$. The radicals $R^{10}$ are preferably hydrogen atoms or $C_1$–$C_{10}$-, preferably $C_1$–$C_4$-alkyl groups.

The particularly preferred metallocenes are thus those in which, in the formula I, $M^1$ is Zr or Hf, $R^1$ and $R^2$ are identical or different and are methyl or chlorine, $R^3$ and $R^4$ are hydrogen, $R^5$ and $R^6$ are identical or different and are methyl, ethyl or trifluoromethyl, $R^7$ is a

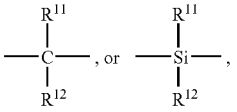

radical, n plus m is zero or 1, and $R^{10}$ is hydrogen; in particular the compounds I listed in the working examples.

Of the metallocenes I mentioned in the working examples, rac-dimethylsilyl(2-methyl-4,5,6,7-tetrahydro-1-indenyl)$_2$zirconium dichloride, rac-ethylene(2-methyl-4,5,6,7-tetrahydro-1-indenyl)$_2$zirconium dichloride, racdimethylsilyl(2-methyl-4,5,6,7-tetrahydro-1-indenyl)$_2$dimethylzirconium and rac-ethylene(2-methyl-4,5,6,7-tetrahydro-1-indenyl)$_2$dimethylzirconium are particularly important.

The chiral metallocenes are employed as racemates for the preparation of highly isotactic poly-1-olefins. However, it is also possible to use the pure R- or S-form. These pure stereoisomeric forms allow the preparation of an optically active polymer. However, the meso form of the metallocenes should be separated off since the polymerization-active center (the metal atom) in these compounds is no longer chiral due to mirror symmetry at the central metal, and it is therefore not possible to produce a highly isotactic polymer.

The principle of resolution of the stereoisomers is known.

The present invention furthermore provides a process for the preparation of the metallocenes I, which comprises a) reacting a compound of the formula II (II)

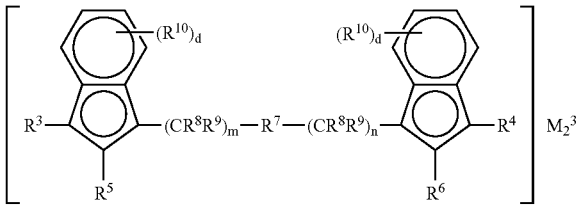

in which $R^3$–$R^{10}$, m and n are defined in the formula I and $M^3$ is an alkali metal, preferably lithium, with a compound of the formula III $M^1X_4$ (III)

in which $M^1$ is a defined in the formula I, and X is a halogen atom, preferably chlorine, and catalytically hydrogenating the reaction product, or b) reacting a compound of the formula IIa (IIa)

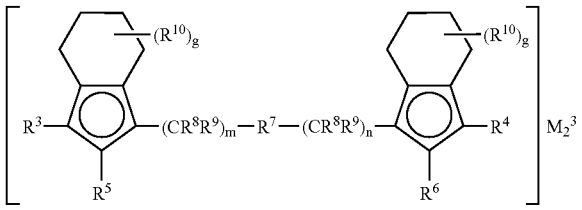

with a compound of the formula III $M^1X_4$ (III)

in which all the substituents are as defined under a), and, if desired, derivatizing the reaction product obtained under a) or b).

The synthesis is carried out under a protective gas and in anhydrous solvents. The dried salt of the formula II/IIa is added to a suspension of the compound of the formula III in a solvent such as toluene, n-hexane, dichloromethane, ether, THF, n-pentane or benzene, preferably dichloromethane or toluene. The reaction temperature is from −78° C. to 30° C., preferably from −40° C. to 10° C. The reaction duration is from 0.25 to 24 hours, preferably from 1 to 4 hours.

A further embodiment of the process according to the invention comprises replacing the compound III, $M^1X_4$, by a compound of the formula IIIa, $M^1X_4L_2$. In this formula, L is a donor ligand. Examples of suitable donor ligands are tetrahydrofuran, diethyl ether, dimethyl ether, inter alia, preferably tetrahydrofuran (THF).

In this case, a solution of the salt of the formula II/IIa in one of the abovementioned solvents is added to a solution or suspension of a compound of the formula IIIa in a solvent such as toluene, xylene, ether or THF, preferably THF. However, an alternative procedure is to simultaneously add both components dropwise to a solvent. This is the preferred procedure. The reaction temperature is from −40° C. to 100° C., preferably from 0° C. to 50° C., in particular from 10° C. to 35° C. The reaction duration is from 0.25 hour to 48 hours, preferably from 1 hour to 24 hours, in particular from 2 hours to 9 hours.

The hydrogenation is carried out in a dry, anhydrous solvent such as $H_2CCl_2$ or glyme. The reaction temperature is 20° to 70° C., preferably from ambient temperature to 50° C., the pressure is from 5 to 200 bar, preferably from 20 to 120 bar, in particular from 35 to 100 bar, and the reaction duration is from 0.25 to 24 hours, preferably from 0.5 to 18 hours, in particular from 1 to 12 hours. Hydrogenation reactors which can be used are steel autoclaves. The hydrogenation catalyst used is platinum, platinum oxide, palladium or another conventional transition-metal catalyst.

The halogen derivatives obtained in this way can be converted into the alkyl, aryl or alkenyl complexes by known standard methods.

The compounds of the formulae II and IIa are synthesized by deprotonation. This reaction is known; cf. J. Am. Chem. Soc., 112 (1990) 2030–2031, ibid. 110 (1988) 6255–6256, ibid. 109 (1987), 6544–6545, J. Organomet. Chem., 322 (1987) 65–70, New. J. Chem. 14 (1990) 499–503 and the working examples.

The synthesis of the protonated forms of the compounds of these formulae has also been described, with the difference that they are not correspondingly substituted in the α- and β-positions (Bull. Soc. Chim., 1967, 2954). The bridging units required for their synthesis are generally commercially available, but the indenyl compounds required, by contrast, are not. Some literature references containing synthesis procedures are indicated; the procedure for indene derivatives which are not mentioned is analogous: J. Org. Chem., 49 (1984) 4226–4237, J. Chem. Soc., Perkin II, 1981, 403–408, J. Am. Chem. Soc., 106 (1984) 6702, J. Am. Chem. Soc., 65 (1943) 567, J. Med. Chem., 30 (1987) 1303–1308, Chem. Ber. 85 (1952) 78–85 and the working examples.

The metallocenes I can thus in principle be prepared in accordance with the reaction scheme below:

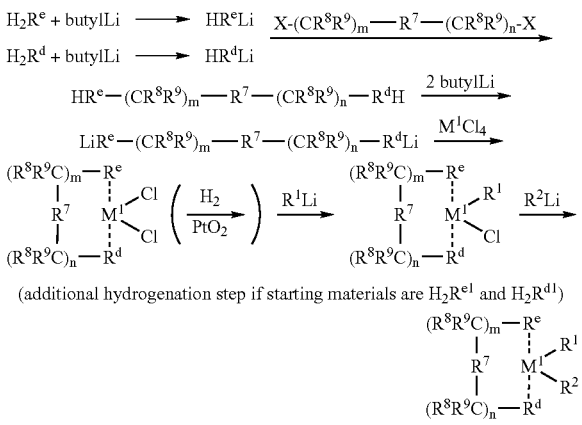

-continued

X = Cl, Br, I, O-tosyl;

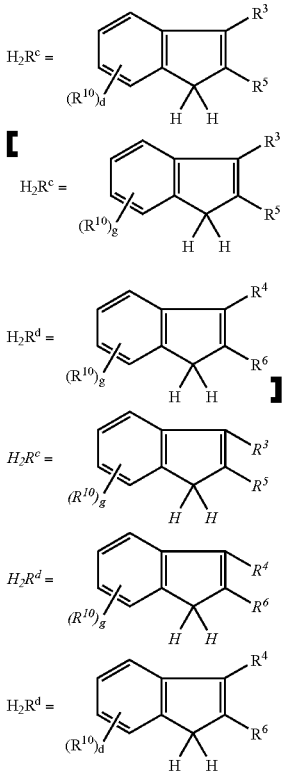

The cocatalyst used according to the invention in the polymerization of olefins is an aluminoxane of the formula (IV)

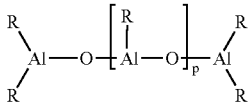

(IV)

for the linear type and/or of the formula (V)

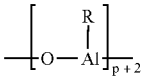

for the cyclic type, where, in the formulae (IV) and (V), the radicals R may be identical or different and are a $C_1$–$C_6$-alkyl group, a $C_6$–$C_{18}$-aryl group or hydrogen, and p is an integer from 2 to 50, preferably from 10 to 35.

The radicals R are preferably identical and are methyl, isobutyl, phenyl or benzyl, particularly preferably methyl.

If the radicals R are different, they are preferably methyl and hydrogen or alternatively methyl and isobutyl, preferably from 0.01 to 40% (of the number of radicals R) being hydrogen or isobutyl.

The aluminoxane can be prepared in different ways by known processes. One of the methods is, for example, the reaction of an aluminium-hydrocarbon compound and/or a hydridoaluminum-hydrocarbon compound with water (gaseous, solid, liquid or bound—for example as water of crystallization) in an inert solvent (such as, for example, toluene). In order to prepare an aluminoxane containing different alkyl groups R, two different trialkylaluminum compounds ($AlR_3$+$AlR'_3$) in accordance with the desired composition are reacted with water (cf. S. Pasynkiewicz, Polyhedron 9 (1990) 429 and EP-A 302 424).

The precise structure of the aluminoxanes IV and V is not known.

Irrespective of the preparation method, a varying content of unreacted aluminum starting compound, in free form or as an adduct, is common to all the aluminoxane solutions.

It is possible to preactivate the metallocene I using an aluminoxane of the formula (IV) and/or (V) before use in the polymerization reaction. This considerably increases the polymerization activity and improves the particle morphology.

The preactivation of the transition-metal compound is carried out in solution. The metallocene is preferably dissolved in a solution of the aluminoxane in an inert hydrocarbon. Suitable inert hydrocarbons are aliphatic or aromatic hydrocarbons. Toluene is preferred.

The concentration of the aluminoxane in the solution is in the range from about 1% by weight up to the saturation limit, preferably from 5 to 30% by weight, in each case based on the entire solution. The metallocene can be employed in the same concentration, but is preferably employed in an amount of from $10^{-4}$–1 mol per mole of aluminoxane. The preactivation time is from 5 minutes to 60 hours, preferably from 5 to 60 minutes. The preactivation temperature is from −78° C. to 100° C., preferably from 0 to 70° C.

The metallocene can also be prepolymerized or applied to a support. The prepolymerization is preferably carried out using the olefin (or one of the olefins) employed in the polymerization.

Examples of suitable supports are silica gels, aluminum oxides, solid aluminoxane or other inorganic support materials. Another suitable support material is a polyolefin powder in finely divided form.

A further possible variation of the process comprises using a salt-like compound of the formula $R_xNH_{4-x}BR'_4$ or of the formula $R_3PHBR'_4$ as cocatalyst instead of or in addition to an aluminoxane. x here is 1, 2 or 3, the R radicals are identical or different and are alkyl or aryl, and R' is aryl, which may also be fluorinated or partially fluorinated. In this case, the catalyst comprises the product of the reaction of a metallocene with one of said compounds (cf. EP-A 277 004).

The polymerization or copolymerization is carried out in a known manner in solution, in suspension or in the gas phase, continuously or batchwise, in one or more steps, at a temperature of from 0° to 150° C., preferably from 30° to 80° C. Olefins of the formula $R^a$—CH═CH—$R^b$ are polymerized or copolymerized. In this formula, $R^a$ and $R^b$ are identical or different and are a hydrogen atom or an alkyl radical having 1 to 14 carbon atoms.

However, $R^a$ and $R^b$, together with the carbon atoms connecting them, may also form a ring. Examples of such olefins are ethylene, propylene, 1-butene, 1-hexene, 4-methyl-1-pentene, 1-octene, norbornene or norbornadiene. In particular, propylene and ethylene are polymerized.

The molecular weight regulator added, if necessary, is hydrogen. The overall pressure in the polymerization system is from 0.5 to 100 bar. The polymerization is preferably carried out in the industrially particularly interesting pressure range of from 5 to 64 bar.

The metallocene is used in a concentration, based on the transition metal, of from $10^{-3}$ to $10^{-8}$, preferably from $10^{-4}$ to $10^{-7}$ mol of transition metal per $dm^3$ of solvent or per $dm^3$ of reactor volume. The aluminoxane is used in a concentration of from $10^{-5}$ to $10^{-1}$ mol, preferably from $10^{-4}$ to $10^{-2}$ mol, per $dm^3$ of solvent or per $dm^3$ of reactor volume. In principle, however, higher concentrations are also possible.

If the polymerization is carried out as a suspension or solution polymerization, an inert solvent which is customary for the Ziegler low-pressure process is used. For example, the polymerization is carried out in an aliphatic or cycloaliphatic hydrocarbon; examples of these which may be mentioned are butane, pentane, hexane, heptane, isooctane, cyclohexane and methylcyclohexane.

It is also possible to use a petroleum ether or hydrogenated diesel oil fraction. Toluene can also be used.

The polymerization is preferably carried out in the liquid monomer.

If inert solvents are used, the monomers are metered in in gaseous or liquid form.

The polymerization can have any desired duration since the catalyst system to be used according to the invention exhibits only a low time-dependent drop in polymerization activity.

The process is distinguished by the fact that the metallocenes according to the invention give, in the industrially interesting temperature range of between 30° and 80° C, polymers of high molecular weight, high stereospecificity, narrow molecular weight dispersity and, in particular, high melting point, which is to say high crystallinity and high hardness.

The examples below are intended to illustrate the invention in greater detail.

The following abbreviations are used:

| | | |
|---|---|---|
| VN = | viscosity number in $cm^3/g$ | |
| $M_w$ = | weight average molecular weight | determined by gel permeation chromatography |
| $M_w/M_n$ = | molecular weight dispersity | determined by gel permeation chromatography |
| II = | isotactic index (II = mm + ⅛ ms), determined by $^{13}$C-NMR spectroscopy | |
| $n_{iso}$ = | length of the isotactic blocks (in propylene units) ($n_{iso}$ = 1 + 2 mm/mr), determined by $^{13}$C-NMR spectroscopy | |

The melting points and heats of melting $\Delta H_{melt}$ were determined using DSC (heating and cooling rate 20° C./min).

Synthesis of the starting substances

I) Synthesis of 2-Me-indene 110.45 g (0.836 mol) of 2-indanone were dissolved in 500 ml of diethyl ether, and 290 $cm^3$ of 3N (0.87 mol) ethereal methylGrignard solution were added dropwise at such a rate that the mixture refluxed gently. After the mixture had boiled for 2 hours under gentle reflux, it was transferred onto an ice/hydrochloric acid mixture, and a pH of 2–3 was established using ammonium chloride. The organic phase was separated off, washed with $NaHCO_3$ and sodium chloride solution and dried, giving 98 g of crude product (2-hydroxy-2-methylindane), which was not purified further.

This product was dissolved in 500 $cm^3$ of toluene, 3 g of p-toluenesulfonic acid were added, and the mixture was heated on a water separator until the elimination of water was complete, and was evaporated, the residue was taken up in dichloromethane, the dichloromethane solution was filtered through silica gel, and the filtrate was distilled in vacuo (80° C./10 mbar).

Yield: 28.49 g (0.22 mol/26%).

The synthesis of this compound is also described in: C. F. Koelsch, P. R. Johnson, J. Am. Chem. Soc., 65 (1943) 567–573.

II) Synthesis of (2-Me-indene)$_2$SiMe$_2$ 13 g (100 mmol) of 2-Me-indene were dissolved in 400 cm$^3$ of diethyl ether, and 62.5 cm$^3$ of 1.6N (100 mmol) n-butyllithium/n-hexane solution were added dropwise over the course of 1 hour with ice cooling, and the mixture was then stirred at ~35° C. for a further 1 hour.

6.1 cm$^3$ (50 mmol) of dimethyldichlorosilane were introduced into 50 cm$^3$ of Et$_2$O, and the lithio salt solution was added dropwise at 0° C. over the course of 5 hours, the mixture was stirred overnight at room temperature and left to stand over the weekend.

The solid which had deposited was filtered off, and the filtrate was evaporated to dryness. The product was extracted using small portions of n-hexane, and the extracts were filtered and evaporated, giving 5.7 g (18.00 mmol) of white crystals. The mother liquor was evaporated, and the residue was then purified by column chromatography (n-hexane/H$_2$CCl$_2$ 9:1 by volume), giving a further 2.5 g (7.9 mmol/52%) of product (as an isomer mixture).

$R_f$(SiO$_2$; n-hexane/H$_2$CCl$_2$ 9:1 by volume)=0.37.

The $^1$H-NMR spectrum exhibits the signals expected for an isomer mixture with respect to shift and integration ratio.

III) Synthesis of (2-Me-Ind)$_2$CH$_2$CH$_2$ 3 g (23 mmol) of 2-Me-indene were dissolved in 50 cm$^3$ of THF, 14.4 cm$^3$ of 1.6N (23.04 mmol) n-butyllithium/n-hexane solution were added dropwise, and the mixture was then stirred at 65° C. for 1 hour. 1 cm$^3$ (11.5 mmol) of 1,2-dibromoethane was then added at −78° C., and the mixture was allowed to warm to room temperature and was stirred for 5 hours. The mixture was evaporated, and the residue was purified by column chromatography (SiO$_2$; n-hexane/H$_2$CCl$_2$ 9:1 by volume).

The fractions containing the product were combined and evaporated, the residue was taken up in dry ether, the solution was dried over MgSO$_4$ and filtered, and the solvent was stripped off.

Yield: 1.6 g (5.59 mmol/49%) of isomer mixture $R_f$(SiO$_2$; n-hexane/H$_2$CCl$_2$ 9:1 by volume)=0.46.

The $^1$H-NMR spectrum corresponds to expectations for an isomer mixture in signal shift and integration.

Synthesis of the metallocenes I

IV) rac-Dimethylsilyl(2-Me-4,5,6,7-tetrahydro-1-indenyl)$_2$zirconium dichloride a. Synthesis of the precursor rac-dimethylsilyl(2-Me-1-idenyl)$_2$zirconium dichloride 1.68 g (5.31 mmol) of the chelate ligand dimethylsilyl(2-methylindene)$_2$ were introduced into 50 cm$^3$ of THF, and 6.63 cm$^3$ of a 1.6N (10.61 mmol) n-BuLi/n-hexane solution were added dropwise at ambient temperature over the course of 0.5 hour. The mixture was stirred for 2 hours at about 35° C., the solvent was stripped off in vacuo, and the residue was stirred with n-pentane, filtered off and dried.

The dilithio salt obtained in this way was added at −78° C. to a suspension of 1.24 g (5.32 mmol) of ZrCl in 50 cm$^3$ of CH$_2$Cl$_2$, and the mixture was stirred at this temperature for 3 hours. The mixture was then warmed to room temperature overnight and evaporated. The $^1$H-NMR spectrum showed, in addition to the presence of some ZrCl$_4$(thf)$_2$, a rac/meso mixture. After stirring with n-pentane and drying, the solid, yellow residue was suspended in THF, filtered off and examined by NMR spectroscopy. These three working steps were repeated a number of times; finally, 0.35 g (0.73 mmol/14%) of product was obtained in which the rac form, according to $^1$ H-NMR, was enriched to more than 17:1.

The compound exhibited a correct elemental analysis and the following NMR signals (CDCl$_3$, 100 MHz): δ=1.25 (s, 6H, Si-Me); 2.18 (s, 6H, 2-Me); 6.8 (s, 2H, 3-H-Ind); 6.92–7.75 (m, 8H, 4-7-H-Ind).

b. Synthesis of the end product 0.56 g (1.17 mmol) of the precursor rac-dimethylsilyl(2-Me-1-indenyl)$_2$zirconium dichloride were dissolved in 70 cm$^3$ of CH$_2$Cl$_2$ and the solution was introduced, together with 40 mg of PtO$_2$, into a 200 cm$^3$ NOVA stirred autoclave. The mixture was then stirred at room temperature for 4 hours under an H$_2$pressure of 40 bar. The filtrate was evaporated, the residue was washed with toluene/n-hexane (1:2 by volume), filtered and evaporated. N-pentane was added, and the suspension obtained was filtered off and dried. The yield was 0.34 g (0.7 mmol/60%). The $^1$H-NMR spectrum (CD$_2$Cl$_2$, 100 MHz) showed the following signals:

δ=0.90 (s, 6H, Me-Si); 1.43–1.93 (m, 8H, indenyl-H); 2.10 (s, 6H, 2-Me); 2.44–3.37 (m, 8H, indenyl-H); 6.05 (s, 2H, 3-H-Ind).

V) Synthesis of rac-ethylene(2-Me-4,5,6,7-tetrahydrol-indenyl)$_2$zirconium dichloride a. Synthesis of the precursor rac-ethylene(2-Me-1-indenyl)$_2$zirconium dichloride 14.2 cm$^3$ of 2.5N (35.4 mmol) n-BuLi/n-hexane solution were added dropwise over the course of 1 hour at room temperature of 5.07 g (17.7 mmol) of the ligand ethylene (2-methylindene)$_2$ in 200 cm$^3$ of THF, and the mixture was then stirred at about 50° C. for 3 hours. A precipitate which formed temporarily dissolved again. The mixture was left to stand overnight.

6.68 g (17.7 mmol) of ZrCl$_4$(thf)$_2$ in 250 cm$^3$ of THF were added dropwise, simultaneously with the above dilithio salt solution, to about 50 cm$^3$ of THF at 50° C., and the mixture was then stirred at this temperature for 20 hours. The toluene extract of the evaporation residue was evaporated. The residue was extracted with a little THF, and the product was recrystallized from toluene, giving 0.44 g (0.99 mmol/5.6%) of product in which the rac form was enriched to more than 15.1.

The compound exhibited a correct elemental analysis and the following NMR signals (CDCl$_3$, 100 MHz): δ=2.08 (2s, 6H, 2-Me); 3.45–4.18 (m, 4H, —CH$_2$C—H$_2$—); 6.65 (2H, 3-H-Ind); 7.05–7.85 (m, 8H, 4-7-H-Ind).

b. Synthesis of the end product 56 g (1.25 mmol) of rac-ethylene(2-Me-1-indenyl)$_2$-zirconium dichloride was dissolved in 50 cm$^3$ of CH$_2$Cl$_2$, and the solution was introduced, together with 40 mg of PtO$_2$, into a 200 cm$^3$ NOVA stirred autoclave. The mixture was then stirred at room temperature for 2 hours under an H$_2$ pressure of 40 bar and evaporated to dryness, and the residue was sublimed in a high vacuum at a bath temperature of about 100° C., giving 0.46 g (1.01 mmol/81%) of product. The elemental analysis was correct, and the $^1$H-NMR spectrum showed the following signals: δ=1.46–1.92 (m, 8H, indenyl-H), 2.14 (s, 6H, 2-Me); 2.49–2.73 (m, 6H, indenyl-H and —CH$_2$CH$_2$—), 2.89–3.49 (m, 6H, indenyl-H); 6.06 (s, 2H, 3-H-Ind).

VI) Me$_2$Zr[(2-Me-4,5,6,7-H$_4$-Ind)$_2$CH$_2$CH$_2$]

5 cm$^3$ of 1.6N (8 mmol) of ethereal methyllithium solution were added dropwise at −50° C. to 1.27 g (2.79 mmol) of Cl$_2$Zr[(2-Me-4,5,6,7-H$_4$-Ind)$_2$CH$_2$CH$_2$] in 20 cm$^3$ of Et$_2$O, and the mixture was then stirred for 1 hour at −10° C. The solvent was replaced by n-hexane, and the mixture was stirred for a further 2 hours at room temperature, filtered and evaporated.

Yield: 1 g (2.40 mmol/86%); correct elemental analysis.

VII) Me$_2$Zr[(2-Me-4,5,6,7-H$_4$-Ind)$_2$SiMe$_2$]

4.3 cm$^3$ of 1.6N (6.88 mmol) of ethereal methyllithium solution were added dropwise over the course of 15 minutes at −35° C. to 1.33 g (2.74 mmol) of Cl$_2$Zr[(2-Me-4,5,6,7-H$_4$-Ind)$_2$SiMe$_2$] in 25 cm$^3$ of Et$_2$O. The mixture was stirred for 1 hour, the solvent was replaced by n-hexane, the mixture was stirred for 2 hours at 10° C. and then filtered, the filtrate was evaporated, and the residue was sublimed in a high vacuum.

Yield: 1.02 g (2.49 mmol/89%); correct elemental analysis.

VIII) $Cl_2Zr[(2\text{-Me-}4,5,6,7\text{-}H_4\text{-Ind})_2SiMePh]$ 1.5 g (2.78 mmol) of $Cl_2Zr[(2\text{-Me-Ind})_2SiMePh]$ and 60 mg of $PtO_2$ in 80 $cm^3$ of $H_2CCl_2$ were hydrogenated for 5 hours at 40° C. in a stirred autoclave under an $H_2$ pressure of 30 bar. The mixture was filtered, the solvent was stripped off, and the residue was sublimed in a high vacuum.

Yield: 0.71 g (1.30 mmol/47%); correct elemental analysis.

IX) $Cl_2Zr[(2\text{-Me-}4,5,6,7\text{-}H_4\text{-Ind})_2SiPh_2]$ 0.8 g (1.33 mmol) of $Cl_2Zr[(2\text{-Me-Ind})_2SiPh_2]$, dissolved in 50 $cm^3$ of $H_2CCl_2$, were stirred for 3 hours at 40° C. with 30 mg of Pt under an $H_2$ pressure of 50 bar. The mixture was filtered, the filtrate was evaporated, the residue was washed with warm n-hexane, the mixture was filtered, and the filtrate was evaporated.

Yeild: 0.36 g (0.59 mmol/44%); correct elemental analysis.

X) $Cl_2Zr[(2\text{-Et-}4,5,6,7\text{-}H_4\text{-Ind})_2CH_2CH_2]$ 1.09 g (2.30 mmol) of $Cl_2Zr[(2\text{-Et-Ind})_2CH_2CH_2]$ in 80 $cm^3$ of $H_2CCl_2$ were hydrogenated for 1 hour at ambient temperature together with 50 mg of $PtO_2$ under an $H_2$ pressure of 80 bar. The mixture was filtered, the filtrate was evaporated, and the residue was sublimed in a high vacuum.

Yield: 0.94 g (1.95 mmol/85%); correct elemental analysis.

XI) $Cl_2Zr[(2\text{-Et-}4,5,6,7\text{-}H_4\text{-Ind})_2SiMe_2]$ 2.00 g (3.96 mmol) of $Cl_2Zr[(2\text{-Et-Ind})_2SiMe_2]$in 100 $cm^3$ of $H_2CCl_2$ were hydrogenated for 3 hours at 35° C. together with 60 mg of $PtO_2$ under an $H_2$ pressure of 50 bar. The mixture was filtered, the filtrate was evaporated, and the residue was recrystallized from n-pentane.

Yield: 1.41 g (2.75 mmol/69%); correct elemental analysis.

XII) $Cl_2Zr[(2\text{-Me-}4,5,6,7\text{-}H_4\text{-Ind})_2CHMeCH_2]$ 0.80 g (1.73 mmol) of $Cl_2Zr[(2\text{-Me-Ind})_2CHMeCH_2]$ in 40 $cm^3$ of $H_2CCl_2$ were stirred for 1 hour at ambient temperature together with 30 mg of $PtO_2$ under an $H_2$ pressure of 80 bar, the mixture was then filtered, the filtrate was evaporated, and the residue was sublimed.

Yield: 0.55 g (1.17 mmol/68%); correct elemental analysis.

XIII) $Cl_2Zr[(2\text{-Me-}4,5,6,7\text{-}H_4\text{-Ind})_2CMe_2]$ 0.3 g (0.65 mmol) of $Cl_2Zr[(2\text{-Me-Ind})_2CMe_2]$ in 30 $cm^3$ of $H_2CCl_2$ were hydrogenated for 1 hour at ambient temperature together with 30 mg of Pt under an $H_2$ pressure of 70 bar. The solvent was stripped off, and the residue was sublimed in a high vacuum.

Yield: 0.21 g (0.45 mmol/69%); correct elemental analysis

Abbreviations:

Me=methyl, Et=ethyl, Bu=butyl, Ph=phenyl,

Ind=indenyl, THF=tetrahydrofuran, PP=polypropylene,

PE=polyethylene.

Metallocenes I as catalysts for the polymerization of olefins.

Example 1

12 $dm^3$ of liquid propylene were introduced into a dry 24 $dm^3$ reactor which had been flushed with nitrogen. 35 $cm^3$ of a toluene solution of methylaluminoxane (corresponding to 52 mmol of Al, mean degree of oligomerization n=17) were then added, and the batch was stirred at 30° C. for 15 minutes. In parallel, 5.3 mg (0.011 mmol) of rac-dimethylsilyl(2-Me-4,5,6,7-tetrahydro-1-indenyl)$_2$zirconium dichloride were dissolved in 13.5 $cm^3$ of a toluene solution of methylaluminoxane (20 mmol of Al) and preactivated by standing for 15 minutes. The solution was then introduced into the reactor and the polymerization system was heated to 70° C. (over the course of 5 minutes) and kept at this temperature for 3 hours by cooling.

The activity of the metallocene was 50.3 kg of PP/g of metallocene×h.

VN=37 $cm^3/g$; $M_w$=24 300 g/mol; $M_w/M_n$=2.4; II=96.0%; $n_{iso}$=62; M.p.=150° C.; $\Delta H_{melt}$=104 J/g.

Example 2

Example 1 was repeated, but 19.5 mg (0.04 mmol) of the metallocene were employed, and the polymerization temperature was 50° C.

The activity of the metallocene was 18.8 kg of PP/g of metallocene×h.

VN=72 $cm^3/g$; $M_w$=64 750 g/mol; $M_w/M_n$=2.1; II=96.0%; $n_{iso}$=64; M.p.=154° C.; $\Delta H_{melt}$=109.5 J/g.

Example 3

Example 1 was repeated, but 58.0 mg (0.12 mmol) of the metallocene were used and the polymerization temperature was 30° C.

The activity of the metallocene was 9.7 kg of PP/g of metallocene×h.

VN=152 $cm^3/g$; $M_w$=171 000 g/mol; $M_w/M_n$=2.2; II=99.9%; $n_{iso}$=>500; M.p.=160° C.; $\Delta H_{melt}$=103 J/g.

Comparative Examples A–H

Examples 1 to 3 were repeated, but the metallocenes dimethylsilyl(2-Me-1-indenyl)$_2$zirconium dichloride (metallocene 1 ), dimethylsilyl(4,5,6,7-tetrahydro-1-indenyl)$_2$zirconium dichloride (metallocene 2) and dimethylsilyl(1-indenyl)$_2$zirconium dichloride (metallocene 3) were used.

| Comp. Ex. | Metallocene | Polym. temp. [° C.] | $n_{iso}$ | M.p. [° C. ] | $\Delta H_{meh}$ [J/g] |
|---|---|---|---|---|---|
| A | 1 | 70 | 38 | 145 | 86.6 |
| B | 1 | 50 | 48 | 148 | 88.1 |
| C | 1 | 30 | 48 | 152 | 90.2 |
| D | 2 | 70 | 34 | 141 | — |
| E | 2 | 50 | 38 | 143 | — |
| F | 3 | 70 | 32 | 140 | — |
| G | 3 | 50 | 34 | 142 | — |
| H | 3 | 30 | 37 | 145 | — |

Comparison of Comparative Examples F/G with D/E confirms the positive effect of the 4,5,6,7-tetrahydroindenyl ligand compared with indenyl, and Comparative Examples F/G/H compared with A/B/C show the positive effect of the substitution in the 2-position of the indenyl ligand.

In comparison with Examples 1 to 3, however, only the combination of substitution in the 2-position together with the tetrahydroindenyl system results in very high melting points and heats of melting and thus in high crystallinity and hardness of the polymers.

Example 4

Example 1 was repeated, but 6.8 mg (0.015 mmol) of ethylene(2-Me-4,5,6,7-tetrahydro-1-indenyl)$_2$zirconium dichloride were employed.

The metallocene activity was 72.5 kg of PP/g of metallocene×h.

VN=35 cm$^3$/g; $M_w$=20 750 g/mol; $M_w/M_n$=1.9; II=94.5%; $n_{iso}$=34; M.p.=141° C.; $\Delta H_{melt}$=92.4 J/g.

Example 5

Example 4 was repeated, but 28.1 mg (0.062 mmol) of the metallocene were used and the polymerization temperature was 50° C.

The metallocene activity was 28.5 kg of PP/g of metallocene×h.

VN=51 cm$^3$/g; $M_w$=28 200 g/mol; $M_w/M_n$=2.2; II=94.8%; $n_{iso}$=35; M.p.=143° C.; $\Delta H_{melt}$=97.9 J/g.

Example 6

Example 4 was repeated, but 50 mg (0.110 mmol) of the metallocene were used and the polymerization temperature was 30° C.

The metallocene activity was 10.9 kg of PP/g of metallocene×h.

VN=92 cm$^3$/g; $M_w$=93 800 g/mol; $M_w/M_n$=2.2; II=95.5%; $n_{iso}$=48; M.p.=151° C.; $\Delta H_{melt}$=99.0 J/g.

Comparative Examples I–O

Examples 4 to 6 were repeated, but the metallocenes ethylene(1-indenyl)$_2$zirconium dichloride (metallocene 4) and ethylene(2-Me-1-indenyl)$_2$zirconium dichloride (metallocene 5) were used.

| Comp. Ex. | Metallocene | Polym. temp. [° C.] | $n_{iso}$ | M.p. [° C. ] | $\Delta H_{meh}$ [J/g] |
|---|---|---|---|---|---|
| I | 4 | 70 | 23 | 132 | 64.9 |
| K | 4 | 50 | 30 | 138 | 78.1 |
| L | 4 | 30 | 29 | 137 | 78.6 |
| M | 5 | 70 | 25 | 134 | 77.0 |
| N | 5 | 50 | 30 | 138 | 78.9 |
| O | 5 | 30 | 32 | 138 | 78.6 |

Comparison of Comparative Examples I to O with Examples 4 to 6 confirms the effect of the substitution in the 2-position together with the use of the tetrahydroindenyl system. $n_{iso}$, melting point and heat of melting are significantly higher in each of Examples 4–6, and the crystallinity and hardness of the polymers are thus also significantly improved.

We claim:

1. A compound of the formula I for preparing essentially isotactic olefin polymers (I)

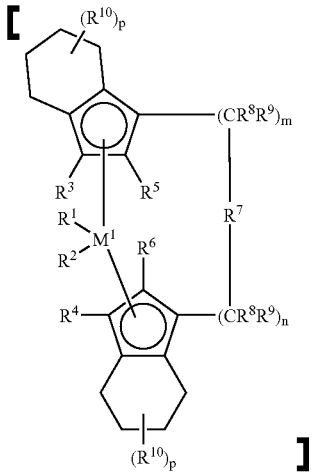

*(I)*

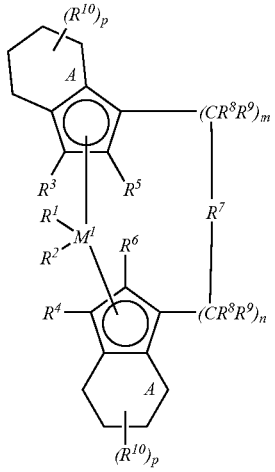

in which $M^1$ is a metal from group IVb, Vb or VIb of the Periodic Table $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom,

*$R^3$ is a hydrogen atom, a halogen atom, a $C_2$–$C_{10}$-alkyl group, a $C_1$–$C_{10}$-alkyl group which is halogenated, a $C_6$–$C_{10}$-aryl group, an —$NR_2^{15}$, —$SR^{15}$, —$OSiR_3^{15}$, —$SiR_3^{15}$ or —$PR_2^{15}$ radical in which $R^{15}$ is a halogen atom, a $C_1$–$C_{10}$-alkyl group or a $C_6$–$C_{10}$-aryl group,*

[$R^3$ and] $R^4$ [are identical or different and are] *is* a hydrogen atom, a halogen atom, a $C_1$–$C_{10}$-alkyl group, which is optionally halogenated, a $C_6$–$C_{10}$-aryl group, an —$NR_2^{15}$, —$SR^{15}$, —$OSiR_3^{15}$, —$SiR_3^{15}$ or —$PR_2^{15}$ radical in which $R^{15}$ is a halogen atom, a $C_1$–$C_{10}$-alkyl group or a $C_6$–$C_{10}$-aryl group, $R^5$ and $R^6$ are identical or different and are as defined for [$R^3$ and] $R^4$, with the proviso that $R^5$ and $R^6$ are not hydrogen, $R^7$ is

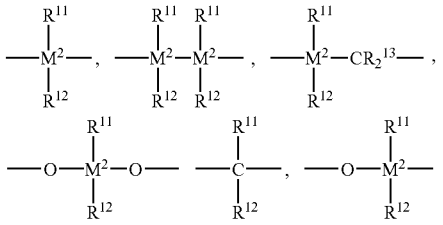

$=BR^{11}$, $=AlR^{11}$, —Ge—, —Sn—, —O—, —S—, =SO, $=SO_2$, $=NR^{11}$, =CO, $=PR^{11}$ or $=P(O)R^{11}$, where $R^{11}$, $R^{12}$ and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or *a pair of substituents* $R^{11}$ and $R^{12}$ or $R^{11}$ and $R^{13}$ in each case with the atoms connecting them, form a ring, $M^2$ is silicon, germanium or tin, $R^8$ and $R^9$ are identical or different and are as defined for $R^{11}$ m and n are identical or different and are zero, 1 or 2, m plus n being zero, 1 or 2, the radicals $R^{10}$ are identical or different and are as defined for $R^{11}$, $R^{12}$ and $R^{13}$,

*rings A are saturated or aromatic,*

*p is 8, when rings A are saturated, and*

*p is 4, when rings A are aromatic.*

2. A compound of the formula I as claimed in claim 1, wherein, in the formula I, $M^1$ is Zr or Hf, $R^1$ and $R^2$ are identical or different and are methyl or chlorine, $R^3$ or $R^4$ are hydrogen, $R^5$ and $R^6$ are identical or different and are methyl, ethyl or trifluoromethyl, $R^7$ is a

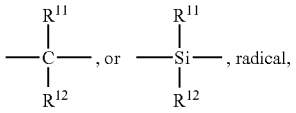

n plus m is zero or 1, and $R^{10}$ is hydrogen.

3. A compound of the formula I as claimed in claim 1 wherein the compound is rac-dimethylsilyl(2-methyl-4,5,6,7-tetrahydro-1-indenyl)$_2$zirconium dichloride, racethylene (2-methyl-4,5,6,7-tetrahydro-1-indenyl)$_2$zirconium dichloride, rac-dimethylsilyl (2-methly-4,5,6,7-tetrahydro-1-indenyl)$_2$dimethylzirconium or racethylene(2-methyl-4,5,6,7-tetrahydro-1-indenyl)$_2$dimethylzirconium.

4. A compound as claimed in claim 1, wherein $M^1$ is zirconium, hafnium or titanium.

5. A compound as claimed in claim 1, wherein $R^1$ and $R^2$ are identical or different and are a hydrogen atom, a $C_1$–$C_3$-alkyl group, a $C_1$–$C_3$-alkoxy group, a $C_6$–$C_8$-aryl group, a $C_6$–$C_6$-arloxy group, a $C_2$–$C_4$-alkenyl group, a $C_7$–$C_{10}$-arylalkyl group, a $C_7$–$C_{12}$-alkylaryl group, a $C_8$–$C_{12}$-arylalkenyl group or chlorine.

6. A compound as claimed in claim 1, wherein $R^3$ *is a $C_4$-alkyl group, $C_1$–$C_4$-alkyl group which is halogenated, a $C_6$–$C_8$-aryl group, an $—NR_2^{15}$, $—SR^{15}$, $—OSiR_3^{15}$, $—SiR_3^{15}$ or $—PR_2^{15}$ radical* and $R^4$ [are identical and different and are] *is* a hydrogen atom, a fluorine, chlorine or bromine atom, a $C_1$–$C_4$-alkyl group, which may be halogenated, a $C_6$–$C_8$-aryl group, an $—NR_2^{15}$, $—SR^{15}$, $—OSiR_3^{15}$, $—SiR_3^{15}$ or $—PR_2^{15}$ radical in which $R^{15}$ is a chlorine atom, or a $C_1$–$C_3$-alkyl group or a $C_6$–$C_8$-aryl group.

7. A compound [as claimed in claim 1,] *of the formula (I)for preparing essentially isotactic olefin polymers*

*(I)*

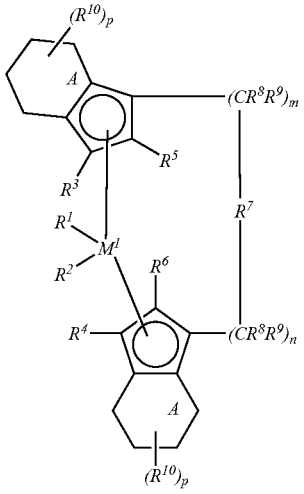

*in which*

*$M^1$ is a metal from group IVb, Vb or VIb of the Periodic Table*

*$R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom,*

$R^3$ and $R^4$ are hydrogen,

*$R^5$ and $R^6$ are identical or different and are a halogen atom, a $C_1$–$C_{10}$-alkyl group, which is optionally halogenated, a $C_6$–$C_{10}$-aryl group, an $—NR_2^{15}$, $—SR^{15}$, $—OSiR_3^{15}$, $—SiR_3^{15}$ or $—PR_2^{15}$ radical in which $R^{15}$ is a halogen atom, a $C_1$–$C_{10}$-alkyl group or a $C_6$–$C_{10}$-aryl group*

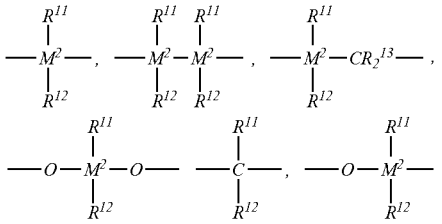

*$=BR^{11}$, $=AlR^{11}$, —Ge—, —Sn—, —O—, —S—, =SO, $=SO_2$, $=NR^{11}$, =CO, $=PR^{11}$ or $=P(O)R^{11}$, where*

*$R^{11}$, $R^{12}$ and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or a pair of substituents $R^{11}$ and $R^{12}$ -- or $R^{11}$ and $R^{13}$ in each case with the atoms connecting them, form a ring,*

*$M^2$ is silicon, germanium or tin,*

*$R^8$ and $R^9$ are identical or different and are as defined for $R^{11}$*

*m and n are identical or different and are zero, 1 or 2, m plus n being zero, 1 or 2,*

*the radicals $R^{10}$ are identical or different and are as defined for $R^{11}$, $R^{12}$ and $R^{13}$,*

*rings A are saturated or aromatic,*

*p is 8, when rings A are saturated, and*

*p is 4, when rings A are aromatic.*

8. A compound as claimed in claim 1, wherein $R^5$ and $R^6$ are identical.

9. A compound as claimed in claim 1, wherein $R_5$ and $R_6$ are ($C_1$–$C_4$)-alkyl, which may be halogenated with methyl.

10. A compound as claimed in claim 1, wherein $R^{11}$, $R^{12}$ and $R^{13}$ are identical or different and are a hydrogen atom, a halogen atom, a $C_1$–$C_4$-alkyl group, a $CF_3$ group, a $C_6$–$C_8$-aryl group, a pentafluorophenyl group, a $C_1$–$C_4$-alkoxy group, a $C_2$–$C_4$-alkenyl group, a $C_7$–$C_{10}$-arylalkyl group, a $C_8$–$C_{12}$-arylalkenyl group of a $C_7$–$C_{12}$-alkylaryl group, or $R^{11}$ and $R^{12}$ or $R^{11}$ and $R^{13}$, in each case together with the atoms connecting them, form a ring.

11. A compound as claimed in claim 1, wherein $M^2$ is silicon or germanium.

12. A compound as claimed in claim 1, wherein $R^7$ is $=CR^{11}R^{12}$, $=SiR^{11}R^{12}$, $=GeR^{11}R^{12}$, —O—, —S—, =SO, $—PR^{11}$ or $=P(O)R^{11}$.

13. A compound as claimed in claim 1, wherein m and n are identical or different and are zero or 1.

14. A compound as claimed in claim 1, wherein m plus n is zero or 1.

15. A compound as claimed in claim 1, wherein $R^{10}$ is hydrogen or $C_1$–$C_4$-alkyl groups.

*16. A compound of the formula (I)'*

*(I)'*

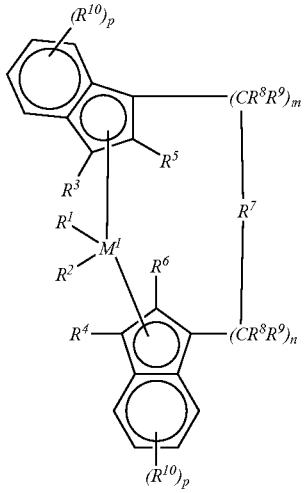

*in which*

*$M^1$ is a metal from group IVb, Vb or VIb of the Periodic Table,*

*$R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom,*

*$R^3$ is a hydrogen atom, a halogen atom, a $C_2$–$C_{10}$-alkyl group, a $C_1$–$C_{10}$-alkyl group which is halogenated, a $C_6$–$C_{10}$-aryl group, an $—NR_2^{15}$, $—SR^{15}$, $—OSiR_3^{15}$, $—SiR_3^{15}$ or $—PR_2^{15}$ radical in which $R^{15}$ is a halogen atom, a $C_1$–$C_{10}$-alkyl group or a $C_6$–$C_{10}$-aryl group,*

*$R^4$ is a hydrogen atom, a halogen atom, a $C_1$–$C_{10}$-alkyl group, which is optionally halogenated, a $C_6$–$C_{10}$-aryl group, an $—NR_2^{15}$, $—SR^{15}$, $—OSiR_3^{15}$, $—SiR_3^{15}$ or $—PR_2^{15}$ radical in which $R^{15}$ is a halogen atom, a $C_1$–$C_{10}$-alkyl group or a $C_6$–$C_{10}$-aryl group,*

*$R^5$ and $R^6$ are identical or different and are as defined for $R^3$ and $R^4$, with the proviso that $R^5$ and $R^6$ are not hydrogen,*

*$R^7$ is*

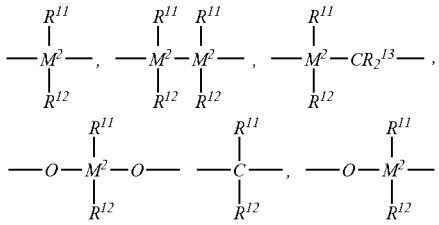

*$=BR^{11}$, $=AlR^{11}$, —Ge—, —Sn—, —O—, —S—, =SO, $=SO_2$, $=NR^{11}$, =CO, $=PR^{11}$ or $=P(O)R^{11}$,*

*where*

*$R^{11}$, $R^{12}$ and $R^{13}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or a pair of substituents $R^{11}$ and $R^{12}$ or $R^{11}$ and $R^{13}$, in each case with the atoms connecting them, form a ring,*

*$M^2$ is silicon, germanium or tin,*

*$R^8$ and $R^9$ are identical or different and are as defined for $R^{11}$*

*m and n are identical or different and are zero, 1 or 2, m plus n being zero, 1 or 2, the radicals $R^{10}$ are the same or different and are as defined for $R^{11}$, $R^{12}$ and $R^{13}$.*

*17. A compound as claimed in claim 16, wherein:*

*$M^1$ is titanium, zirconium, hafnium, vanadium, niobium, or tantalum,*

*$R^1$ and $R^2$ are identical or different and are methyl or halogen,*

*$R^3$ and $R^4$ are hydrogen,*

*$R^5$ and $R^6$ are identical or different and are methyl, ethyl, or trifluoromethyl,*

*$R^7$ is a radical of the formula*

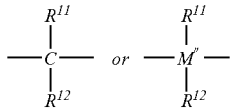

*where $M^{11}$ is silicon or germanium, and*

*$R^8$ and $R^9$ are identical or different and are hydrogen or $C_1$–$C_{10}$-alkyl.*

*18. A catalyst composition comprising the combination comprising a compound of claim 16 and a cocatalyst.*

*19. A catalyst composition comprising the combination comprising a compound of claim 16 and an aluminoxane.*

*20. A process for polymerizing an olefin monomer, comprising the step of carrying out the polymerization in the presence of a catalyst composition of claim 19.*

*21. A process for polymerizing an olefin monomer, comprising the step of carrying out the polymerization in the presence of a catalyst composition of claim 20.*

*22. The compound as claimed in claim 1, wherein $R^3$ is a hydrogen atom, a halogen atom, a $C_1$–$C_{10}$-alkyl group which is halogenated, a $C_6$–$C_{10}$-aryl group, an —$NR_2^{15}$, —$SR^{15}$, —$OSiR_3^{15}$, —$SiR_3^{15}$ or —$PR_2^{15}$ radical in which $R^{15}$ is a halogen atom, a $C_1$–$C_{10}$-alkyl group or a $C_6$–$C_{10}$-aryl group.*

*23. The compound as claimed in claim 1, wherein $R^3$ is a hydrogen atom, a halogen atom, a $C_6$–$C_{10}$-aryl group, an —$NR_2^{15}$, —$SR^{15}$, —$OSiR_3^{15}$, —$SiR_3^{15}$ or —$PR_2^{15}$ radical in which $R^{15}$ is a halogen atom, a $C_1$–$C_{10}$-alkyl group or a $C_6$–$C_{10}$-aryl group.*

* * * * *

UNITED STATES PATENT AND TRADEMARK OFFICE

CERTIFICATE OF CORRECTION

PATENT NO. : RE 39,561 E
APPLICATION NO. : 08/895950
DATED : April 10, 2007
INVENTOR(S) : Andreas Winter It is certified that error appears in the above-identified patent and that said Letters Patent is hereby corrected as shown below:

Title Page; item (57);

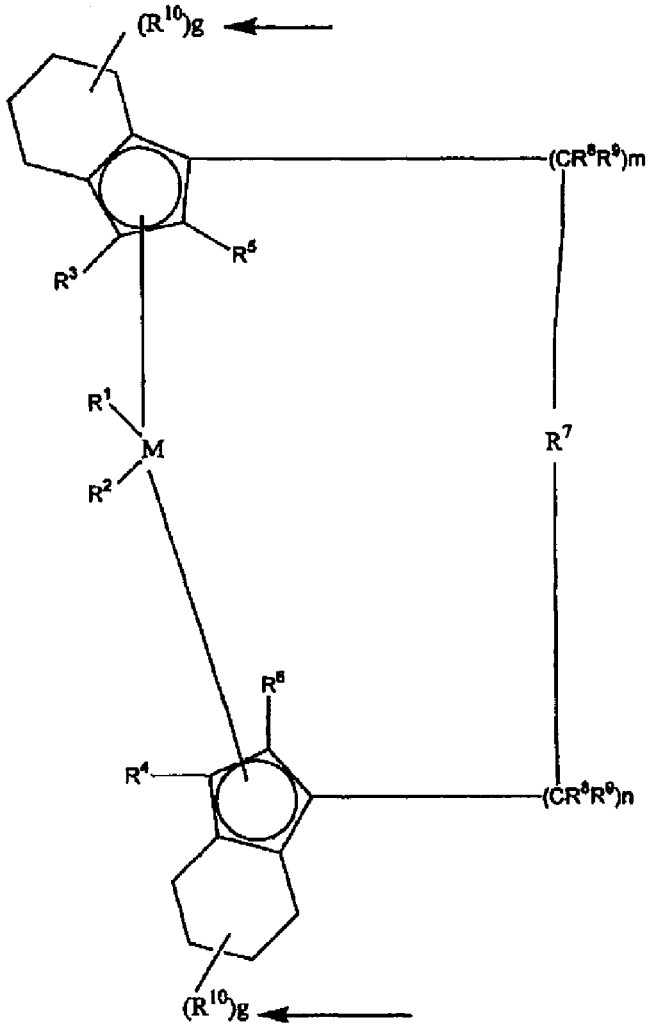

(I)

" " should read

UNITED STATES PATENT AND TRADEMARK OFFICE

CERTIFICATE OF CORRECTION

PATENT NO. : RE 39,561 E
APPLICATION NO. : 08/895950
DATED : April 10, 2007
INVENTOR(S) : Andreas Winter It is certified that error appears in the above-identified patent and that said Letters Patent is hereby corrected as shown below:

--

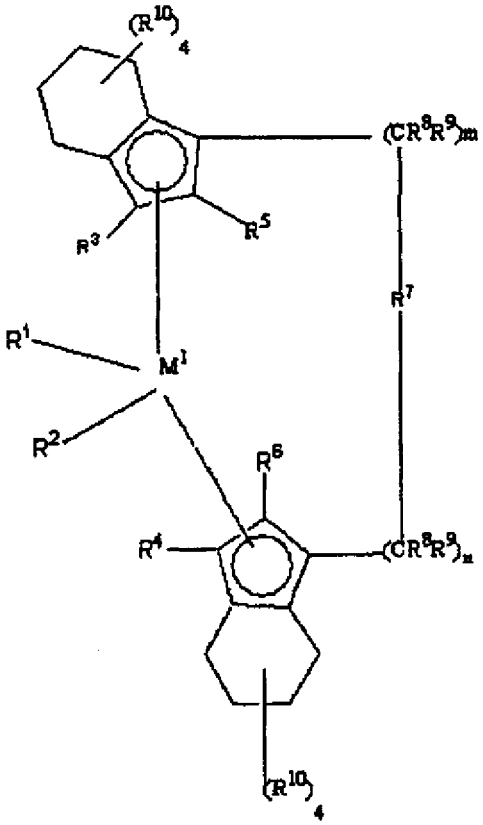

(I)

--.

In the Claims:

In Claim 1, in column 14, on line 59, "hydrogen atom, a halogen atom, a $C_1$-$C_{10}$ –alkyl group," should read -- hydrogen atom, [a halogen atom,] a $C_1$-$C_{10}$ –alkyl group, --.

UNITED STATES PATENT AND TRADEMARK OFFICE

CERTIFICATE OF CORRECTION

PATENT NO. : RE 39,561 E
APPLICATION NO. : 08/895950
DATED : April 10, 2007
INVENTOR(S) : Andreas Winter It is certified that error appears in the above-identified patent and that said Letters Patent is hereby corrected as shown below:

In Claim 16, in column 17, on line 37

" 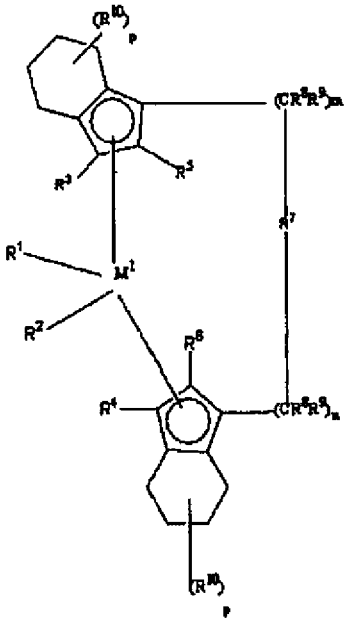 (I) " should read

-- 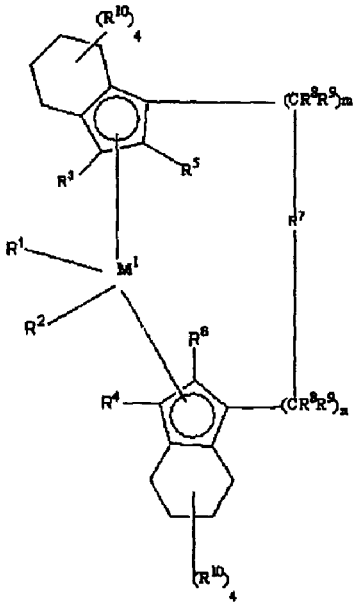 (I) --.

UNITED STATES PATENT AND TRADEMARK OFFICE

CERTIFICATE OF CORRECTION

PATENT NO. : RE 39,561 E
APPLICATION NO. : 08/895950
DATED : April 10, 2007
INVENTOR(S) : Andreas Winter It is certified that error appears in the above-identified patent and that said Letters Patent is hereby corrected as shown below:

In Claim 20, in column 19, on line 3 "presence of a catalyst composition of claim 19", should read -- presence of a catalyst composition of claim 18 --.

In Claim 21, in column 19, on line 7, "presence of a catalyst composition of claim 20", should read -- presence of a catalyst composition of claim 19 --.

Signed and Sealed this

Seventeenth Day of November, 2009

David J. Kappos

David J. Kappos
*Director of the United States Patent and Trademark Office*